United States Patent [19]
Atkins et al.

[11] Patent Number: 5,665,093
[45] Date of Patent: Sep. 9, 1997

[54] SURGICAL IMPLANTATION METHOD AND APPARATUS

[76] Inventors: Joseph R. Atkins, 2190 Little York Rd., Dayton, Ohio 45414; Vakeriy Moysaenko, 1185 Hillcrest Dr., Troy, Ohio 45323

[21] Appl. No.: 735,204

[22] Filed: Oct. 21, 1996

Related U.S. Application Data

[63] Continuation-in-part of Ser. No. 570,772, Dec. 11, 1995, abandoned.

[51] Int. Cl.$^6$ ............................................. A61F 11/00
[52] U.S. Cl. ........................ 606/108; 606/1; 606/159; 606/185
[58] Field of Search .................... 606/108, 1, 167, 606/170, 159, 185, 188, 184, 222–228; 604/165, 164; 128/749, 760

[56] References Cited

U.S. PATENT DOCUMENTS

| | | | |
|---|---|---|---|
| 460,138 | 9/1891 | Hornberger | 606/188 |
| 518,600 | 4/1894 | Hallman | 606/170 |
| 2,568,207 | 9/1951 | Spicher | 606/188 |
| 2,713,863 | 7/1955 | Handerson | 606/188 |
| 4,382,444 | 5/1983 | Malmin | 606/187 |
| 5,191,898 | 3/1993 | Millar | 128/748 |
| 5,203,863 | 4/1993 | Bidoia | 606/1 |
| 5,314,435 | 5/1994 | Green et al. | 606/1 |
| 5,356,419 | 10/1994 | Chow | 606/170 |
| 5,382,251 | 1/1995 | Hood et al. | 606/99 |
| 5,382,257 | 1/1995 | Lewis et al. | 606/224 |

FOREIGN PATENT DOCUMENTS

| | | | |
|---|---|---|---|
| 37701 | 12/1886 | Germany | 606/185 |

*Primary Examiner*—Robert A. Hafer
*Assistant Examiner*—Justine R. Yu
*Attorney, Agent, or Firm*—Richard W. Lavin

[57] ABSTRACT

An apparatus and method for implanting within a human or animal body a surgical device which includes a tubular member with outside markings having a removable pointed end member mounted in the front end of the tubular member; a rod member slidably mounted within the tubular member and a removable handle member secured to the rear end of the tubular member. A pair of incision are made in the body adjacent the area in which the surgical device is to be implanted. The assembled device is inserted in one incision until the pointed end protrudes through the second incision. The pointed end member and the hand handle member are then removed. One end of the implantable surgical device is then attached to one end of the rod member which is then withdrawn from the tubular member together with the surgical device until the surgical device is properly positioned in the tissue. Once the rod member and one end of the surgical device has been withdrawn through the tubular member, the surgical device is removed, from the rod member. The surgeon stabilizes the surgical device at the second incision by holding one of the free ends of the surgical device. The tubular member is then withdrawn from the body leaving the surgical device in the desired implanted area.

15 Claims, 8 Drawing Sheets

SURGICAL IMPLANTATION METHOD AND APPARATUS

RELATED APPLICATION DATA

Continuation-in-part of Ser. No. 08/570,772, filed Dec. 11,1995, now abandoned.

BACKGROUND OF THE INVENTION

The present invention is directed to the implanting of surgical devices and more particularly to a method of and apparatus for the surgical implantation of graft, catheters, as we'll as cables or wires, optic fibers or any straight or curve, stiff, flexible or semi-flexible materials into living tissue. For example, arterial or venous grafts and catheters implanted for the purpose of arterio-venous bypass or extra corporeal therapies of any kind are presently being implanted into living tissue with the aid of a large Kelly forceps or solid barb-tipped trocar. The problem with the use of Kelly clamps are that they are designed for clamping heavy tissue, gauze and surgical towels. They were never intended to produce tunnels or to act as a tunneling device in living tissue for implanting graft, catheters or other stiff, flexible or non-flexible medical or veterinary devices. Typically, the surgeon takes the pointed end of the Kelley damp and forces it through the living tissue until the blunt end of the clamp is protruding through to the desired incision. The Kelly damp is then opened. The surgical device is grasped by the jagged edges of the clamp and is then dragged back through the living tissue. The oversized and irregular tunnel left by the Kelly damp is always uneven, which can cause the surgical device not to seat properly in the tissue. The improper seating of the surgical device can eventually lead to infection and or failure of the implanted surgical device.

As for barbed trocars with sharp tips, they am nothing more than large sewing needles which the surgeon uses to bore through tissue. Once the opposing incision is reached, the surgical device is attached to the barbed end and the surgical device is pulled back through the tissue. The tunnel made by the trocar is often too tight, inhibiting proper seating of the surgical device.

In the end, use of beth of the above mention devices can lead to misplacement and kinking of implanted graft and catheters as well as an increased infection and increased mortality rate for human, as well as animal subjects.

It is therefor a principal object of the present invention to provide a method and apparatus for implanting a surgical device into human or animal tissue which over comes the problem of infection, excessive tissue trauma, and poor seating of surgical devices in living tissue.

It is another object of the present invention to provide a method and apparatus for implanting a surgical device into human and animal tissue which is simple in construction and therefore low in cost.

It is another object of the present invention to provide a method and apparatus for accurately implanting a surgical device into human and animal tissue.

SUMMARY OF THE INVENTION

There is provided, in accordance with the present invention, a method and apparatus for implanting into human tissue a surgical device such as; natural or artificial arterial/vascular graft, catheters, cables, wires, sutures, cords, optic fibers, metal/plastic/or composite material rods, or any other extra corporeal/biomedical device. The apparatus comprises a tubular member having a removable pointed front end member for penetrating living tissue. The tubular member had etched on its outer surface a plurality of locating marks which may comprise a metric ruler. Slidably mounted within the tubular member is a rod member having connecting means on its tip and a holding member mounted on its opposite end enabling the rod to be withdrawn from the tubular member for seating the surgical device in the intended position within the living tissue. A handle member is removably secured to the rear end of the tubular member opposite the pointed end member enabling the tubular member to be pushed through the tissue, in the operation of the apparatus, a first incision is made in the tissue and a second incision is made at the expected distal exit site. The operator then Inserts the pointed end member of the tubular member into the first incision site, pushing the apparatus through the tissue utilizing the handle member until the pointed end member extends through the second incision site is reached. Upon protrusion through the second insertion site, the operator removes the pointed end member from the front end of the tubular member and the handle member from the rear end of the tubular member. The rod member is then partially removed from the tubular member so that it is freed and loose, but not removed from the barrel housing. The surgical device which is to be inserted into the tissue is attached to the front end of the rod. The operator then withdraws the rod member through the tubular member while applying a backward movement to the tubular member until the surgical device is centered exactly where it is suppose to be. Once that point has been reached the implanted surgical device is then removed from the end of the rod. The operator then grasps the free end of the surgical device at the second incision site, stabilizing it, and then removes the tubular member from the tissue until it has cleared the tissue, as well as the implanted surgical device. At this point the surgical device is placed in the optimum position allowing the surgeon to complete the operation with minimal trauma to the patient. If needed, the surgeon may use the locating marks on the tubular member to mark the location of attachments to the surgical device, such as a dacron cuff, which is often used to promote tissue in-growth into device.

BRIEF DESCRIPTION OF THE DRAWING

Additional advantages and meritorious features of the present invention will become more apparent and fully understood from a reading of the following detailed description and appended claims when read in conjunction with the drawings wherein like reference numerals indicate like or corresponding elements throughout the several views and wherein:

DETAILED DESCRIPTION OF THE PREFERRED EMBODIMENT

Figure 1:
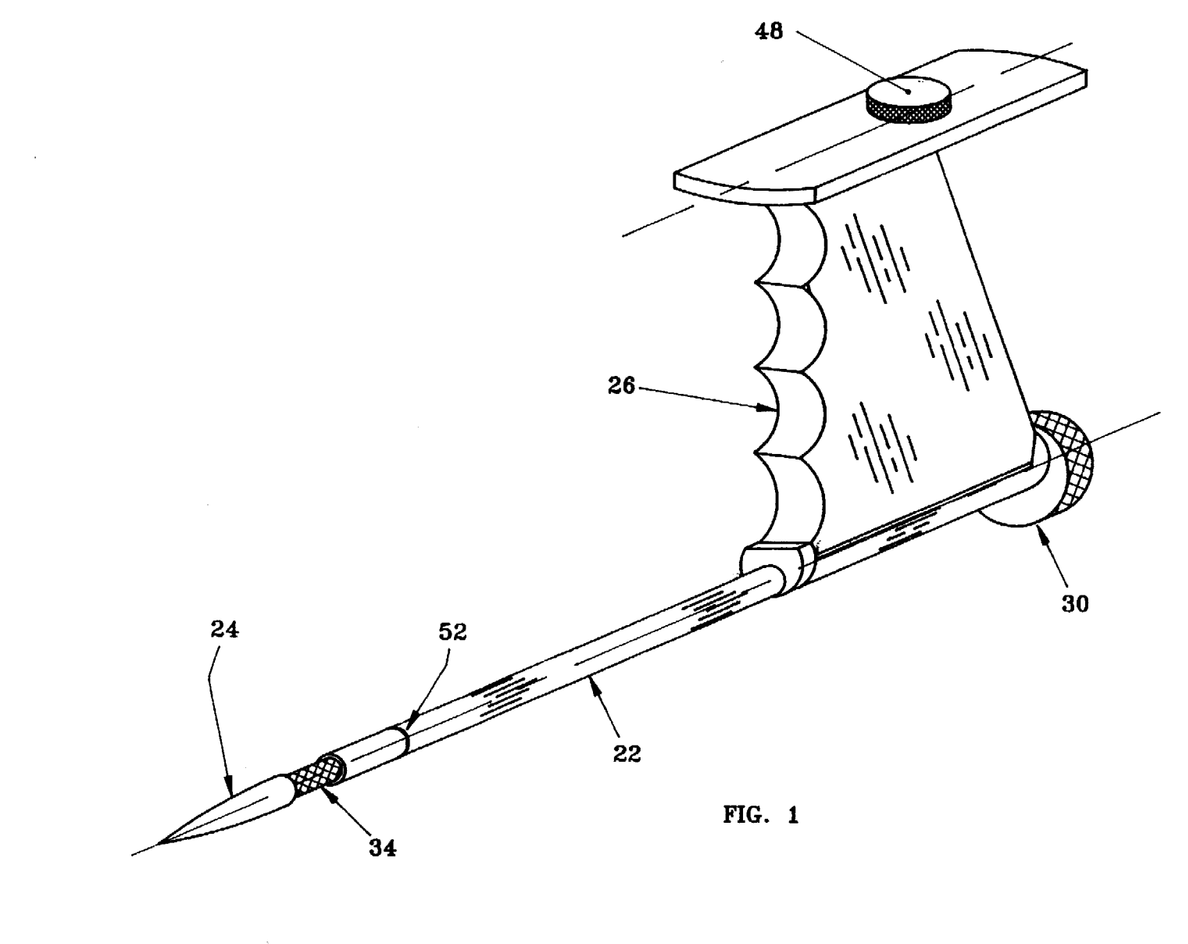
FIG. 1 is a top front perspective view of one embodiment of the implanting apparatus of the present invention.
Figure 2:
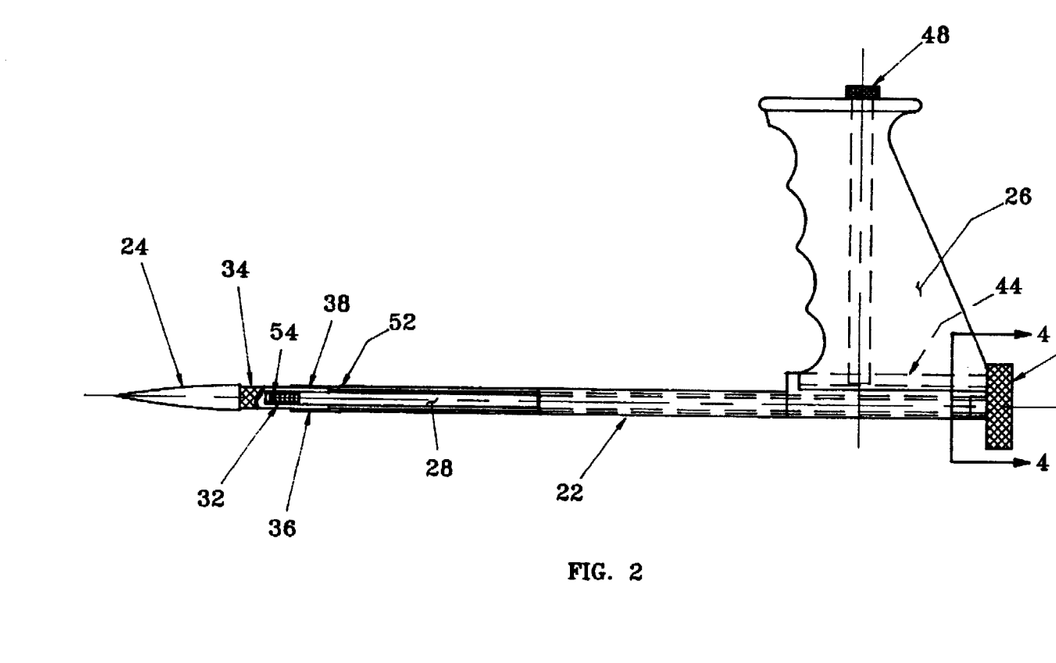
FIG. 2 is a left side view of the implanting apparatus of FIG. 1 with a portion of the tubular body member removed showing details of the forward end of the rod member and its mounting to the tubular body member.
Figure 5:
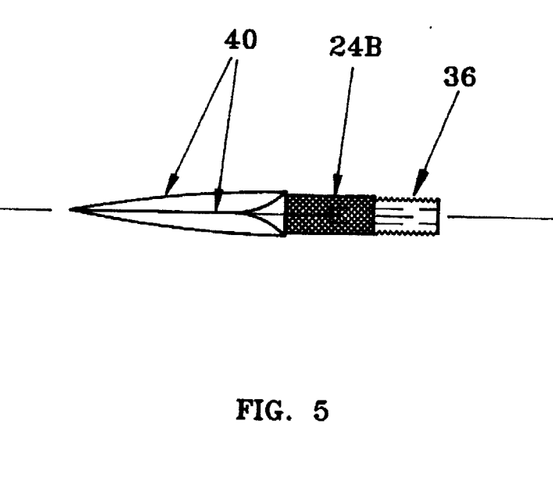
FIG. 5 is a plan view of a second embodiment of the nose portion of the tubular member.
Figure 6:
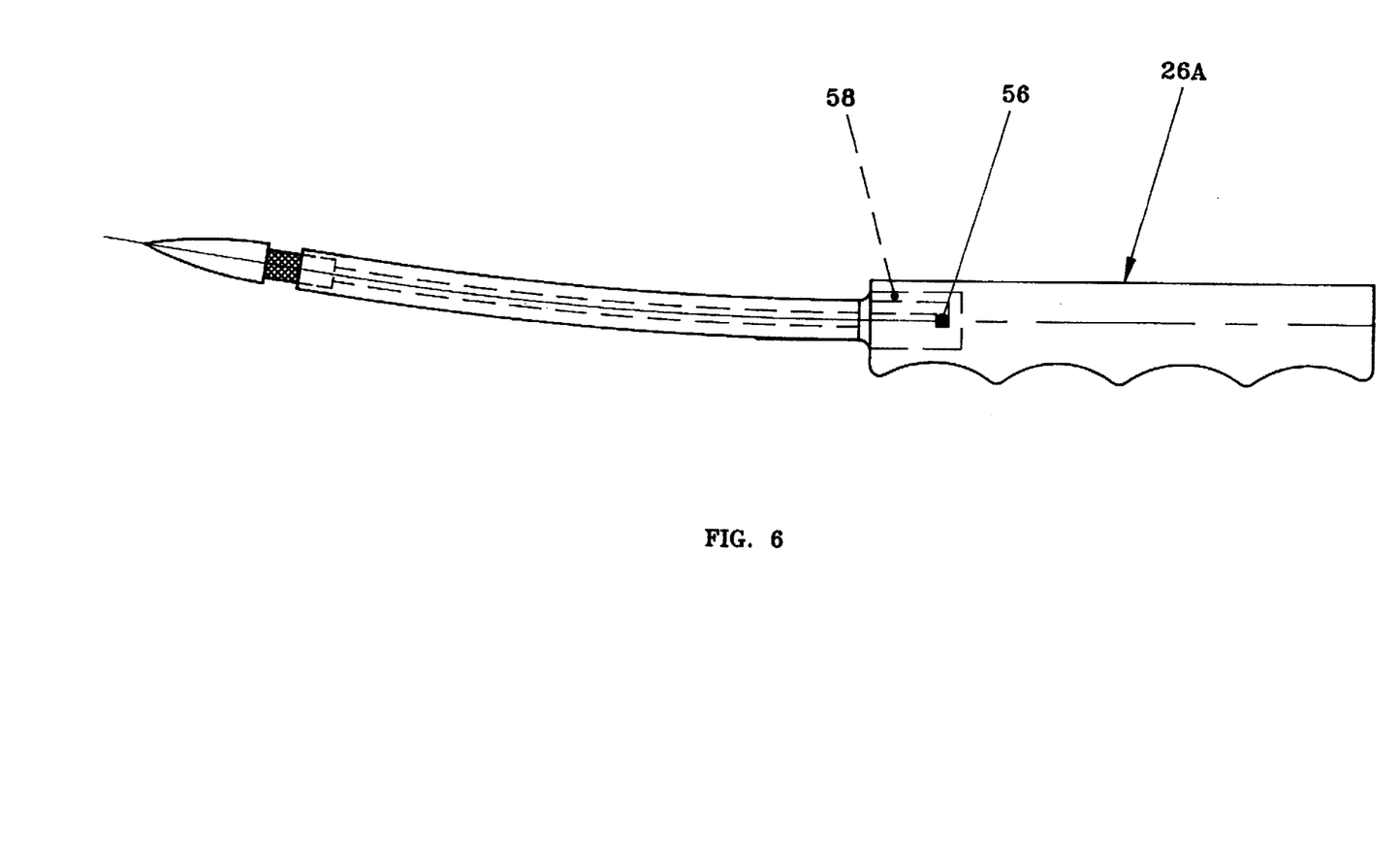
FIG. 6 is a left side view of a second embodiment of the implanting apparatus of the present invention which includes a screw driver type handle member.
Figure 10:
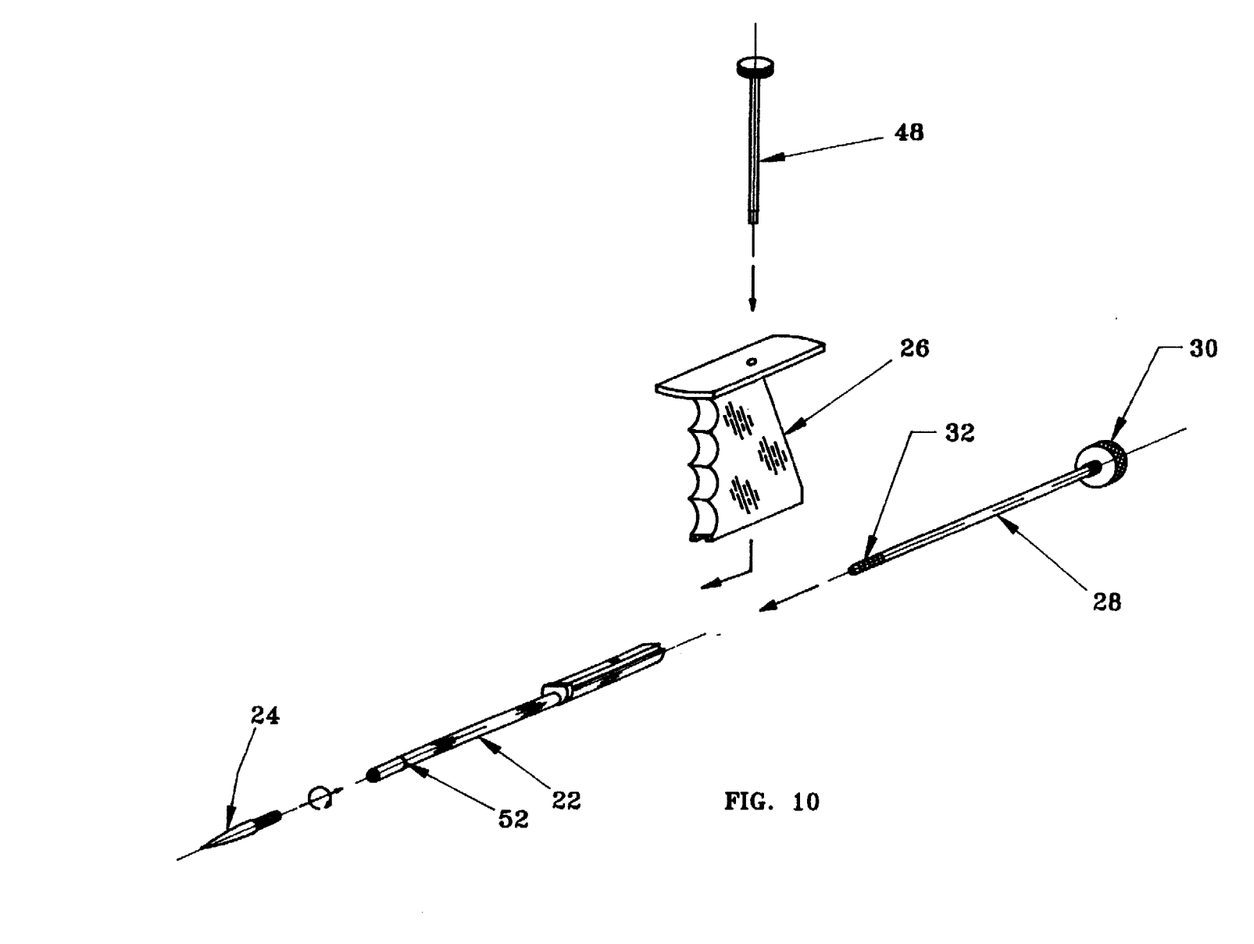
FIG. 10 is an exploded view of the implanting device of FIG. 1.
Figures 11, 12:
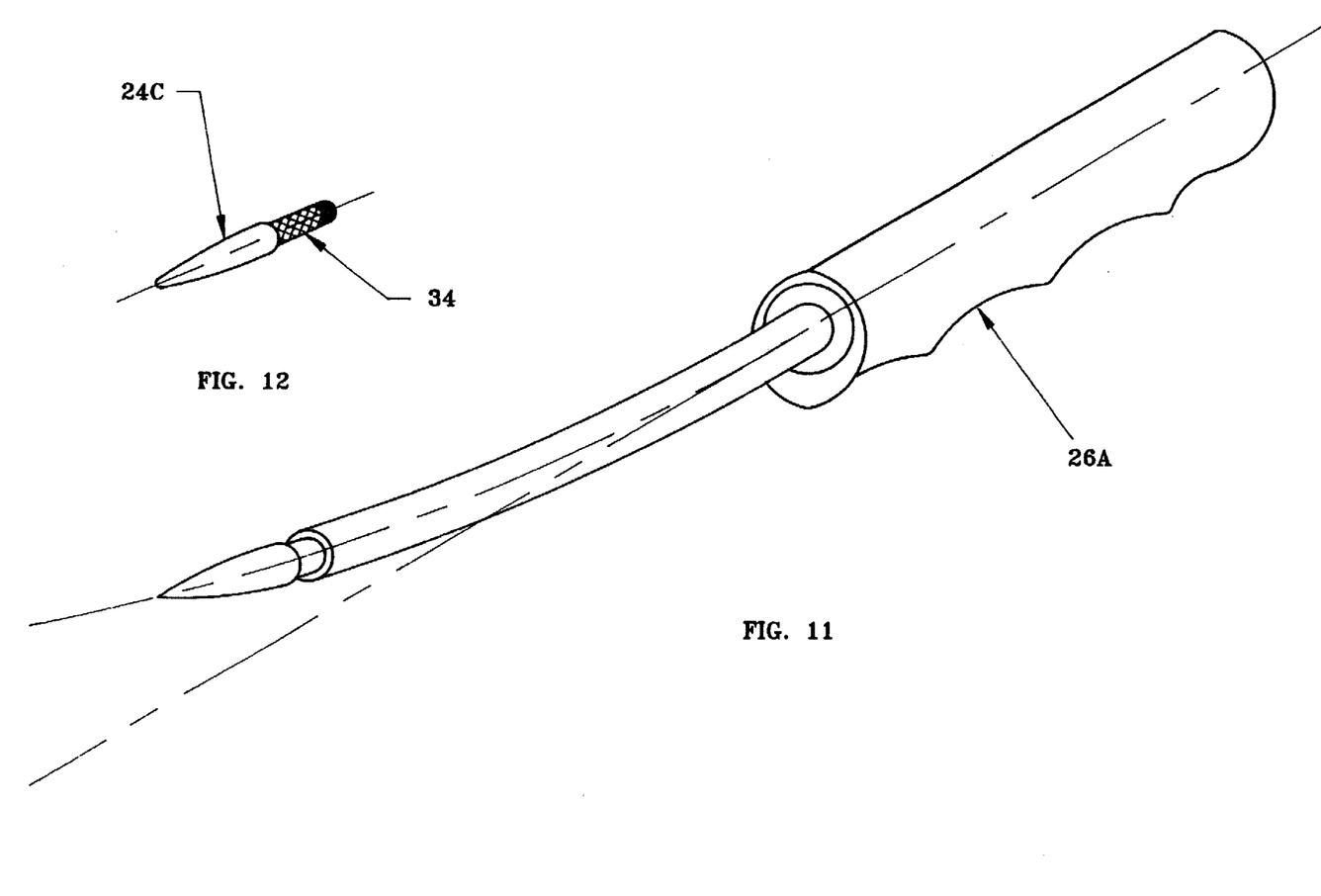
FIG. 11 is a top front perspective view of the implanting apparatus of FIG. 6 showing the curvature of the tubular body member.
FIG. 12 is a top front perspective view of a third embodiment of the removable nose member of the present invention.

Referring now to FIGS. 1 and 2 of the drawings, there is shown a top front perspective view, a side view and an exploded view of the implanting apparatus of the present invention which is generally indicated by the numeral 20 and which includes a tubular body, member 22, a removable nose member 24 and a pistol grip shaped handle member 26 removably secured to the body member. Slidably mounted within the body member 22 is a rod member 28 (FIG. 2) having a knurled knob member 30 secured to its rear end and which is screwed into the rear end of the body member 22. The forward end of the rod member 28 includes a plurality of barb portions 32 allowing the surgical device, which is to be implanted, to be secured to the rod member. The nose member 24 which in the first embodiment (FIGS. 1, 2, and 10) is bullet shaped, includes a knurled portion 34 for grasping the nose portion and an external threaded portion 36 (FIGS. 2 and 5) which is screwed into an internal threaded portion 38 of the body member 22. FIG. 5 shows a second embodiment 24B of the nose member 24 which includes a plurality of cutting edges 40. FIG. 12 shows a third embodiment 24C of the nose member 24 which has blunt nose. The members 22, 26 and 28 may be constructed of any hard plastic or steel material such as spring or tungsten steel. While the shape of the body member 22 is shown to be straight, the present invention may be utilized in a body member which may be curved (FIG. 6).

Figure 3:
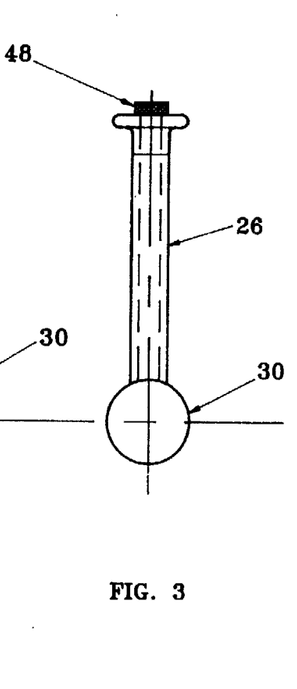
FIG. 3 is rear end view of the implanting apparatus of FIG. 1.
Figure 4:
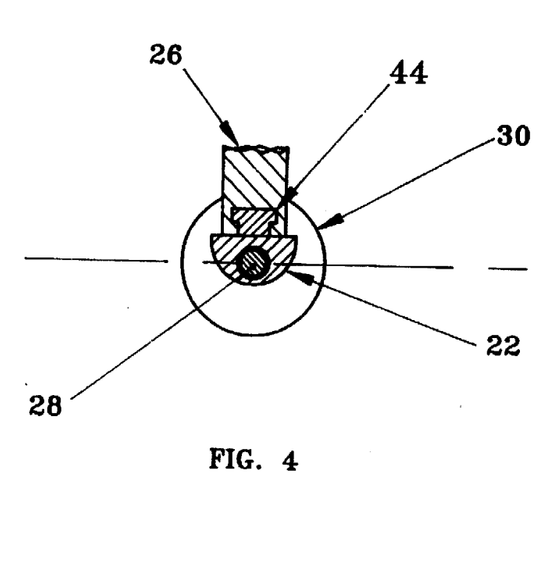
FIG. 4 is a sectional view taken on lines 4—4 of FIG. 1 showing details of the T-rail portion of the tubular member on which the handle is mounted.
Figures 7, 8:
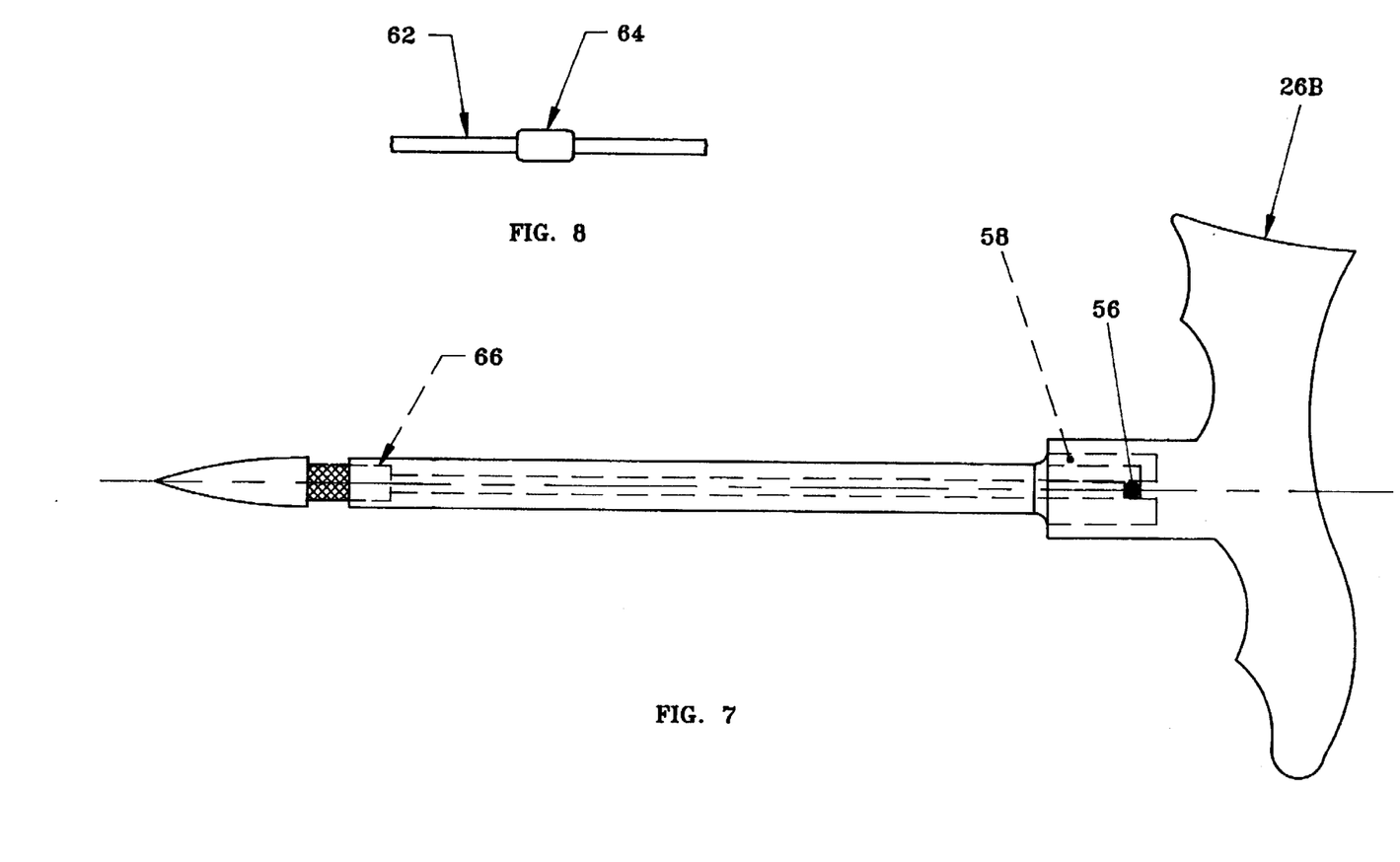
FIG. 7 is a left side view of a third embodiment of the implanting apparatus of the present invention which includes a T-shaped handle member.
FIG. 8 is a plan view of one type of catheter having a dracon cuff which is inserted into the tissue.

Removably secured to the rear portion of the body member 22 is the handle member 26 which is slidably mounted on a T-shaped rail portion 44 (FIGS. 2–4 inclusive) of the body member. The handle member 26 is moved along the rail portion 44 until it engages a stop portion 46 of the body member 22. A bolt member 48 is then inserted through the handle member 26 and screwed into a threaded portion 50 of the rail portion 44 for removably securing the handle member to the body member. FIGS. 7 and 11 disclose two embodiments 26A and 26B of the handle member 26. The handle member 26A (FIG. 7) is shown as a screw-driver shaped handle member while the handle member (FIG. 11) is shown as a T-shaped handle member. The handle members 26A, 26B are secured to the body member 22 using a bayonet type mounting structure which includes a ball bearing member 56 slidably mounted in a slot 58 in a manner that is well known in the art allowing the handle members to be easily removed from the body member when desired.

Figure 9:
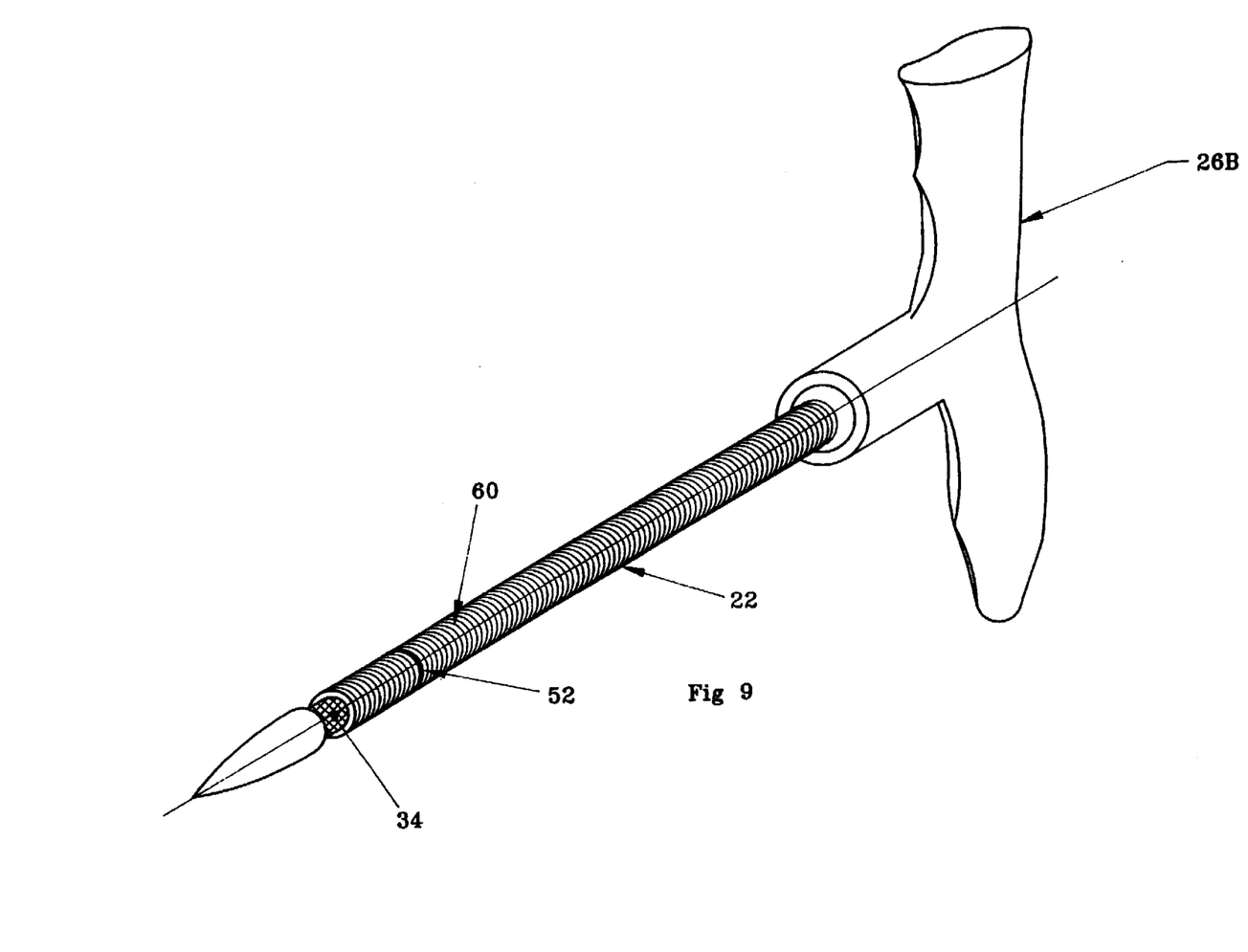
FIG. 9 is a top front perspective view of the implanting apparatus of FIG. 7 showing the location of the cuff warning marker and the printed or etched metric ruler which extends the length of the tubular member.

Referring now to FIG. 8, there is shown a plan view of a catheter 62 in which is located a dacron cuff 64 utilized to promote tissue growth and which is positioned within the tissue of the patient. In order to assist the surgeon in locating the cuff 64 after the catheter 62 has been implanted in the tissue of the patient, there is located on the outside surface of the tubular body member a warning marker 52 (FIGS. 1 and 2) indicating the location of a dacron cuff 64 (FIG. 12) on the catheter. To further assist in locating the cuff 64, a number of metric indicators 60 (FIG. 9) are acid etched on the outside of the tubular member 22 in a manner that is well known in the art. The rod member 28 may also include an eyelet 54 (FIG. 2) through which one end of the surgical device may be inserted for attachment to the rod member. member 28 may also include an eyelet 54 (FIG. 2) through which one end of the surgical device may be inserted for attachment to the rod member.

In the operation of the apparatus, a pair of incisions are made adjacent the area of the body of the patient where the surgical device is to be implanted. The surgeon, utilizing the handle member 26, will insert the nose portion 24 of the body member 22 into one of the incisions and drive the body member through the tissue until it protrudes through the second incision. The nose member 24 is then unscrewed and removed from the body member 22. One end of a surgical device such as the catheter 62 (FIG. 8) is then secured to the barbed portions 32 of the rod member 28. The bolt member 48 is then unscrewed allowing the handle member 26 to be removed. The exposed end of the rod member 28 together with the attached surgical device is then withdrawn from the tubular body member 22 after which the end of the surgical device is removed from the end of the rod member 28 leaving both ends of the surgical device free. Grasping both free ends of the surgical device, the surgical device may be moved to its final position within the tissue utilizing the indicators 60 (FIGS. 1 and 2). Where a dacron cuff 64 (FIG. 8) is involved, the surgeon will feel the cuff during the time the catheter is being pulled through the tissue until the cuff seats in the cuff space 66 (FIG. 7) vacated by the removal of the nose member 24. After the surgical device has been secured, the tubular body member 22 is removed from the tissue. In order to facilitate the movement of the body member 22 through the tissue, the member 22 may be coated with Teflon. Teflon is a registered tradename of the DuPont Corp. Of Wilmington, Del.

It will be seen from this construction that there is provided a method and an apparatus for implanting a surgical device within a patient which is easy In the application, which provides low frictional movement of the device to the implanted position and provides minimum trauma in the patient and while providing maximum accuracy in positioning the surgical device within the patient.

While the salient features of the invention have been illustrated and described, it should be readily apparent to those skilled in the art that many changes and modifications can be made in the invention presented without departing from the spirit and true scope of the invention. Accordingly, the present invention should be considered as encompassing all such changes and modifications of the invention that fall within the broad sense of the invention as defined by the claims.

What is claimed is:

1. An apparatus for implanting a surgical device within the tissue of a patient including:

an elongated hollow member having a front end portion and a rear end portion;

a piercing member removably secured to the front end portion of the hollow member;

a rod member slidably received for movement within the hollow member and extending within the hollow member from the piercing member to a position adjacent the rear end portion of the hollow member;

a surgical device to be implanted within the tissue of a patient;

means located on one end of the rod member for securing one end of the surgical device to the rod member upon removal of the piercing member after the hollow member has been moved through the tissue of the patient to a position where the surgical device is to be implanted:

means removably secured to the other end of the rod member and positioned adjacent the rear end portion of the hollow member for withdrawing the rod member and the attached surgical device through the hollow member to the implanted position when actuated; and drive means removably secured to the rear end portion of the hollow member for driving the hollow member within the tissue of the patient to the implanted position and enabling the rod member and the surgical device to be moved through the hollow member to a position where the device is to be implanted upon removal of the drive means from the hollow member.

2. The implanting apparatus of claim 1 wherein the securing means on said one end of said rod member comprises a plurality of barbed elements upon which one end of the surgical device is attached enabling the rod member to move the surgical device to the implanted area.

3. The implanting apparatus of claim 1 in which said withdrawing means comprises a knob member.

4. The implanting apparatus of claim 1 in which the drive means comprises a handle member.

5. The implanting apparatus of claim 1 in which the drive means comprises a pistol-grip type handle member.

6. The implanting apparatus of claim 1 in which the drive means comprises a screw-driver type handle member.

7. The implanting apparatus of claim 1 in which the drive means comprises a T-shaped handle member.

8. The implanting apparatus of claim 1 in which the piercing member comprises a bullet shaped member having a rear screw portion which is screwed into said hollow member enabling the piercing member to he removed from the hollow member after the hollow member had been moved to the implanted area.

9. The implanting apparatus of claim 1 in which the piercing member comprises bullet shaped member having a blunt front end.

10. The implanting apparatus of claim 1 in which the hollow member includes a plurality of mark indices located along an outer surface of the hollow member for use in locating the hollow member adjacent the implanted area.

11. The implanting apparatus of claim 1 in which the surgical device comprises an elongated catheter having an enlarged portion for promoting the growth of tissue in the implanted area, said hollow member further having a mark located on an outer surface indicating the location of the enlarged portion of the catheter when the catheter is being moved through the hollow member.

12. A method for implanting a flexible surgical device in an implanted position in the tissue of a patient comprising the steps of:

inserting a rigid tube member having a removable piercing pointed front portion, a removable rear end drive portion and a rod member slidably received within the tube member through a first incision in the tissue of the patient located adjacent one side of the implanted position;

moving the tube member using the rear end drive portion through the tissue of the patient and through a second incision located adjacent the other side of the implanted position until the piercing pointed front portion of the tube member protrudes through the second incision;

removing the pointed front portion and the drive portion from the tube member;

attaching one end of a surgical device to one end of the rod member slidably received within the tube member;

moving the rod member and the surgical device through the tube member and through the first incision to the position where the surgical device is to be implanted; and withdrawing the tube member from the tissue while leaving the surgical device in the implanted position.

13. The method of claim 12 in which further includes the step of holding one end of the surgical device before withdrawing the rod member and the surgical device from the tubular member.

14. The method of claim 12 in which the tube member includes an outer surface having a locating mark positioned thereon for use in locating the surgical within the implanted area.

15. The method of claim 12 in which the tube member includes an outer surface having a plurality of locating marks positioned thereon for use in locating the surgical device in the implanted area.

* * * * *